United States Patent [19]
Radman et al.

[11] Patent Number: 5,912,119
[45] Date of Patent: Jun. 15, 1999

[54] PROCESS FOR THE IN VIVO RECOMBINATION OF DNA SEQUENCES HAVING MISMATCHED BASES

[75] Inventors: Miroslav Radman, Paris; Christiane Rayssiguier, Les Ulis, both of France

[73] Assignee: Mixis France, S.A., Paris, France

[21] Appl. No.: 08/231,778

[22] Filed: Apr. 25, 1994

Related U.S. Application Data

[63] Continuation of application No. 07/972,199, Nov. 5, 1992, abandoned, which is a continuation of application No. 07/387,299, Jul. 31, 1989, abandoned.

[30] Foreign Application Priority Data

Dec. 26, 1988 [FR] France ................................ 88 017185

[51] Int. Cl.$^6$ ..................................................... C12Q 1/68
[52] U.S. Cl. ............................................. 435/6; 435/172.3
[58] Field of Search ............................. 435/172.3, 172.1, 435/172.2, 6, 252.3, 254.11, 240.2; 536/23.1

[56] References Cited

PUBLICATIONS

Triaby et al., *J. Bact.*, vol. 121, 1975, pp. 608–618.
Cummins et al., *Gene*, vol. 14, 1981, pp. 263–278.
Smithies et al., *Nature*, vol. 317, 1985, pp. 230–234.
Sanderson et al., *Escherichia coli* and *Salmonella typhimurium*, $2^{nd}$ ed., 1987, pp. 1138–1144.
Cleaver, *Cell*, vol. 76, 1994, pp. 1–4.
Jeyaprakash et al., *Mut. Res.*, vol. 325, 1994, pp.21–29.

*Primary Examiner*—James Ketter
*Attorney, Agent, or Firm*—Foley & Lardner

[57] ABSTRACT

The present invention relates to a process of recombination in vivo of partially homologous DNA sequences having up to 30% of base mismatches. According to its essential characteristic, said sequences are placed together in cells or an organism of which the enzymatic mismatch repair system is defective or has been transitorily inactivated by saturation for the time to obtain recombination between said DNA sequences or in using mutants which increase the intergeneric recombination.

13 Claims, No Drawings

PROCESS FOR THE IN VIVO RECOMBINATION OF DNA SEQUENCES HAVING MISMATCHED BASES

This is a continuation of application Ser. No. 07/972,199, filed Nov. 5, 1992, now abandoned, which in turn is a continuation of Ser. No. 07/387,299, filed Jul. 31, 1989, now abandoned.

BACKGROUND OF THE INVENTION

The present invention relates to a process for the in vivo recombination of homologous DNA sequences but having a considerable proportion of mismatched bases which can range particularly up to 30%.

It is thus possible to recombine individual genes, at the level of cells or of organisms of different species and genera having common ancestors.

The present invention relates also to a process for the production of organisms recombined by crosses and recombination in vivo of different organisms, species and/or genera, as well as a process for the in vivo production of hybrid genes and hence of hybrid proteins coded by the latter.

In the synthesis of DNA, errors can occur and the resulting uncomplementary pairs of bases are called mismatches. A process for the correction of errors (mismatches and non-matches of bases) in DNA, exists. This process brings into action an enzymatic system. Thus, in *Escherichia coli* and *Salmonella typhimurium* bacteria the errors are very rapidly and accurately detected by two enzymes (MutS and MutL) enabling a third enzyme (MutU) to unwind the two DNA strands and a fourth enzyme (MutH) to cut the neosynthesized strand on a sequence of DNA (GATC) itself methylated later by another enzyme (ref: 1). The most frequent errors G:T, A:C and plus or minus one base, are the most effectively repaired. The errors not or poorly detected by the enzymes Mut (G:A, C:T AND C:C in certain places) have a particular structure "opening" the two strands.

Until now, the obtaining of hybrid species or of hybrid genes ran up against numerous problems. As regards hybrid species, the most advanced attempts made in vitro in the vegetable field by fusion of cells ran up against the major problem of genetic instability. As for the obtaining of hybrid genes or enzymes, it was possible only in vitro by genetic engineering.

It is an object of the present invention to form novel hybrid species or, a fortiori, novel hybrid genes or enzymes by in vivo intergeneric and/or interspecific recombinations with increased efficiency and facility.

GENERAL DESCRIPTION OF THE INVENTION

To do this, and according to a first variation of the invention, defective mutants are used in a system of repair of mismatched bases in DNA or any other mutant which increases the intergeneric recombination.

There may be mentioned especially the mut strains, in particular mut L, S, H or U of *Escherichia coli* and *Salmonella typhimurium* or again the hex strains of *Streptococcus pneumoniae* (ref: 2) and pms in yeast (ref: 3).

In fact, it has been discovered according to the invention that the molecular mechanism of speciation, and hence the appearance of a novel species, can critically involve the activity of the enzymes of mismatch correction and only them. The invention consists in fact of exploiting the "anti-recombination" role stimulated by the DNA mismatched bases possessed by the mismatch repair enzymes. This role defines a molecular mechanism of speciation, that is to say of the initial genetic separation of new species.

However, instead of the use of defective mutants in the enzymatic mismatch repair system it is possible to transitorily inactivate this system for a length of time to obtain the desired recombinations, particularly by saturation.

Taking into account the fact that the mismatch repair mutants are genetically unstable, it may be advantageous to use a transitory deficiency necessary to construct the desired genetic structure before coming back to the normal genetic stability. The principal problem in conventional biotechnology is the genetic instability of "industrial" strains. After selection of the desired variant, its own genetic stability is compromised and it reverses towards the wild type in the course of growth in the fermenter.

The strategy for transitory inactivation of the mismatch correction system according to the invention is double:
a) Use of a conditional correction mutant (mutS $^{ts-1}$) of *Escherichia coli* for any genetic construction in *E. coli* and b) Saturation, that is to say functional inactivation of the correction system by introduction into the cell of a large number of mismatches. This method is applicable to any organism whatever.

Accordingly the present invention provides a process of recombination in vivo of DNA sequences homologous but with mismatched bases, characterized in that said sequences are put together in cells or in an organism whose enzymatic repair system is defective or has been transitorily inactivated by saturation for a length of time to obtain recombination between said DNA sequences, or in using mutants which increase the intergeneric recombination.

Therefore, as the case may require, at least one of the enzymes should be inactivated, namely an enzyme involved in the recognition or in the correction error itself.

The DNA sequences concerned for recombination may be chromosomic or extra-chromosomal permitting in the latter case recombination between cloned individual genes.

As an application of this process of in vivo recombination, the present invention also provides a process of production in vivo of hybrid genes and their coded proteins, characterized in that there are placed together in said defective or inactivated organism in the enzymatic mismatch repair system two so-called DNA sequences consisting of partially homologous genes derived from two different organisms, and the desired hybrid gene or its coded protein is selected. In this case it is a matter of extra-chromosomal in vivo production.

It will be possible to introduce, for example, on plasmids the two homologous genes coding for the same function but having a different sequence and quite different enzymatic properties of the product then to select from a Petri dish among the thousands of different recombinations obtained those which could be of interest. This would otherwise correspond to a huge amount of genetic engineering work in vitro.

According to the invention, there is provided a process for the in vivo production of hybrid genes, and of their coded proteins wherein a first gene from a first organism carried on a first plasmid and a second partially homologous gene from a second organism carried on a second plasmid are introduced by transformation in a mismatch repair deficient bacteria or in any other mutant bacteria which increases the intergeneric recombination or in bacteria of which the mismatch repair system is transitorily inactivated and allowed to recombine and wherein the desired hybrid gene or its coded protein is selected.

Particularly in the above process, the bacteria transformed with the plasmids carrying the genes to recombine may be an *E. coli* or *Salmonella typhimurium* strain defective or transitorily inactivated in the enzymatic mismatch repair system or any other mutant of such bacteria which increases the intergeneric recombination.

Advantageously, for any construction in *E. coli,* a thermosensitive strain will be used for the mismatch repair function for example the strain *E. coli* mutS$^{ts-1}$ which is a mutator mutS$^-$ at 42° C. and normal mut$^+$ at 32° C. Heterospecific recombination is activated at 42° C.; the desired character is selected at 32° C.

According to the invention, there is provided as an application of the process of in vivo recombination by transformation or fusion techniques, characterized in that: a transformation and an in vivo recombination is performed:

by means of DNA of cells of an organism of a first species and/or a first genus, with the chromosomal DNA of cells of an organism of a second species and/or of a second genus, these cells of the organism of second species or genus being defective in the enzymatic systems for mismatch repair or having said system transitorily inactivated, particularly by saturation, or the fusion of these two types of cells is performed, the latter having both a defective enzymatic mismatch repair system or having said system inactivated transitorily particularly by saturation and the in vivo recombination of the chromosomes.

According to the invention there is also provided in application of the in vivo process of recombination according to the invention, a process for the production of recombined organisms by cross and recombination in vivo of organisms of different species and/or genera, characterized in that there is carried out a cross and a recombination in vivo between:

an organism of a first species and/or of a first genus, and an organism of a second species and/or of a second genus, one at least of these two organisms being defective in the enzymatic mismatch repair system or having said system transitorily inactivated, particularly by saturation.

In the process of producing cells or recombined organisms according to the invention, it is possible to produce cells or recombined organisms of bacteria, but also of yeasts, of plants or even of animals. In particular, the invention relates to a process for the production of bacteria recombined by cross and recombination of bacteria of different species and/or genera, characterized in that a conjugation or transduction is performed in vivo between so-called recipient bacteria of a first species and/or of a first genus which are defective in enzymatic mismatch repair systems or of which the enzymatic systems of mismatchrepair are transitorily inactivated, particularly by saturation, and so called donor bacteria, of a second species and/or of a second genus which comprise a particular character which it is desired to transfer to the recipient cells.

Advantageously, the so-called recipient bacteria are also defective in the enzymatic restriction systems of the DNA.

The invention manifested itself spectacularly in the field of conjugation of bacteria. The two bacterial genera *Escherichia coli* and *Salmonella typhimurium* which separated genetically some 140 million years ago (Ochman and Wilson 1987) do not cross at all today by recombination of the DNA.

Crosses by conjugation between *Salmonella typhimurium* and *Escherichia coli* are in fact sterile, that is to say recombination is absent or very weak according to the locus concerned (Baron et al. 1959; Eisenstark 1965, Mergeay and Gerits 1983). However, when the functions MutL or MutS for example, are removed by mutations, from these strains there is again obtained, after 140×10$^6$ years, a very effective cross by recombination (at least 10$^6$ times higher than nonmutated bacteria). Thus bacterial crosses bear witness to the role of the repair enzymes in interspecific and intergeneric sterility.

In a particular embodiment of the process of production of recombined bacteria according to the invention, a strain of *E. Coli* and a strain of *Salmonella typhimurium* are crossed, of which one at least is defective or inactivated, particularly by saturation in its enzymatic mismatch repair system.

Preferably, a donor bacterium of the Hfr type will be conjugated with an F$^-$ recipient bacterium.

In a particular embodiment, the conjugation was carried out according to the invention between an Hfr donor *E. Coli* strain and a mutant *Salmonella typhimurium* F$^-$ strain defective for the enzymatic mismatch repair system of the mutS or mutL type, that is to say defective for the proteins MutS and MutL which take part in the recognition of the mismatches.

The process of production of recombined bacteria according to the invention can lead to the manufacture of new strains, for example of attenuated pathogenic Salmonella strains, rendered non toxic by cross with *Esherichia coli* strains but carrying still the antigenic surface determinants of the pathogenic strains, this to produce the vaccine against the corresponding Salmonelloses.

In application of the process of production of recombined organisms according to the invention, there is provided according to the present invention a process for the in vivo production of hybrid genes and of their coded proteins, from two partially homologous genes characterized in that recombined cells are prepared from cells of said first organism which contain a first gene and cells of said second organism which contain a second partially homologous gene, and the desired hybrid gene or its coded protein are selected therefrom.

It is possible, in particular, by using the mismatch repair mutants, to cross bacteria of different origins and thus produce new genes and select the desired properties. In this case they are chromosomal genes.

As mentioned previously, the use of mutants in an enzymatic mismatch repair system can be replaced by the saturation of the enzymatic system by introducing by transfection a heteroduplex of DNA rich in mismatches.

Finally the present invention provides a process of targeted inverse mutagenesis of a gene in an organism said gene comprising a mutated base which it is desired to reestablish as it was before its mutation, characterized in that there is introduced a heteroduplex comprising a high number of mismatches to inactivate by saturation the enzymatic system of mismatch correction of the organism, and an oligonucleotide consisting of the DNA sequence reestablished as it was before mutation of the gene.

According to this process, it is possible to obtain targeted genetic changes with synthetic oligonucleotides by introducing them in large amount into the cells during a period of functional inactivation of the mismatch repair system.

Other advantages and characteristics of the present invention will appear in the light of the examples which follow.

DESCRIPTION OF PREFERRED EMBODIMENTS

EXAMPLE 1

Conjugation between *E. coli* Hfr and *S. typhimurium* F$^-$

Conjugations were made between wild type *E. coli* Hfr and DNA restriction F$^-$ mutant of *S. typhimurium* which were deficient for mismatch repair (mutL, mutS, mutH or mutU).

The transfer origin of the E.coli Hfr strain is at 76.5 min. on the map and xylose is the first marker be injected (78'), The F⁻ Salmonella are double auxotrophs for methionine (met A and met E) and cannot ferment xylose (xyl⁻). They are resistant to streptomycin. The Hfr E. coli is met⁺ and xyl⁺ and sensitive to streptomycin. It is also auxotroph for leucine and threonine which allows a triple counterselection after conjugation. E. coli Hfr and S. typhimurium F⁻ mut⁺, mutL, mutS, mutH or mutU deficient for DNA restriction are grown in rich medium (LB). When they react the log phase (1 to 5 $10^8$/ml) 1 ml of Hfr and 1 ml of F⁻ are mixed and immediately filtered on a millipore filter. This filter is then incubated at 37° C. on a prewarmed rich medium plate. The bacteria are allowed to conjugate for 40 min. and the filter is then put in 1 ml of $MgSO_4$ $10^{-2}M$ and vigorously vortexed for 1' to resuspend the bacteria and separate the conjugants. Aliquots are then plated on selective minimum medium 63 (ref Miller J. H. 72 Experiments in Molecular Genetics (old spring Harbor Laboratory N.Y.) without methionine and with glucose (0.4%) to select for met⁺ recombinants and with xylose as sole carbon source (0.4%) and methionine (100 μg/ml) to select for xyl⁺ recombinants. The two selective media contain neither threonine nor leucine but contain streptomycin (25 μg/ml) to assure a triple counterselection against the Hfr strain. Plates are incubated at 37° C. 40 h, 60 h and 88 h and the recombinant clones counted and studied. A control experiment with the homospecific conjugation Hfr E. Coli X F⁻ E. Coli is done in the same conditions. The recA mutation has been moreover introduced into the F⁻ Salmonella (The recA protein is an indispensable protein for homologous recombination). The results obtained with the mutL and MutS strains for which the effect is the biggest are indicated in Table 1. The frequency per Hfr donor strain of F⁻ recipients which become xyl+ are indicated in the Table 1 (after subtraction of the revertants obtained with the recipient alone incubation 60 h). Equivalent results have been obtained for the met marker.

TABLE 1

| Conjugations | Frequency of xyl⁺/Hfr donor |
| --- | --- |
| Coli Hfr + Coli F⁻ | $1.3\ 10^{-1}$ |
| Coli Hfr + Sal. mut⁺ F⁻ | $6.7\ 10^{-7}$ |
| Coli Hfr + Sal. mutL F⁻ | $2.1\ 10^{-3}$ |
| Coli Hfr + Sal. MutS F⁻ | $1.7\ 10^{-3}$ |
| Coli Hfr + Sal. mut⁺ recA F⁻ | $4.3\ 10^{-8}$ |
| Coli Hfr + Sal. mutL recA F⁻ | $1.8\ 10^{-8}$ |
| Coli Hfr + Sal. MutS recA F⁻ | $6\ 10^{-8}$ |

Intergeneric recombination frequency increases at least $10^4$ fold for mutL and mutS and slightly less for mutH and mut U compared to these observed in conjugations made with F⁻ Salmonella deficient for DNA restriction but wild type for the mismatch repair genes mut⁺. Selecting for recombinants on selective media we were able to get hybrids between E. Coli and S. Typhimurium which we think are new species "Eschenella" or "Salmorichia" with new gene combinations and new recombinant genes.

Prototrophic (met⁺) and sugar fermenting (xyl⁺) products from interspecies recombination could be formed by a variety of mechanism. The simplest is direct gene replacement. The usual outcome of recA-dependent conjugative interactions when E. Coli or S. Typhimurium strains are mated to the recipients of the same species. The two other possible mechanisms lead to the formation of partial diploids. These recombinant types are expected to differ in stability. Simple replacements are expected to be stable whereas partial diploids are expected to be unstable. Therefore, colonies from each cross were checked for phenotypic stability by streaking on indicator plates (1% xylose McConkey medium ref *). Altogether, the stability patterns of the intergeneric recombinants reveal a heterogeneous group.

* Miller, J. H. Experiments in molecular genetics (Cold Spring Harbor Laboratory, Cold Spring Harbor, N.Y., 1972.)

TABLE 2

Analysis of xyl⁺ and metE⁺metA⁺ recombinants from
E. coli Hfr x S. typhimurium F⁻ conjugational crosses

| F⁻ recipient | Coinheritance of markers | | | | xyl⁺ recombinants | |
| --- | --- | --- | --- | --- | --- | --- |
| | % met⁺ among xyl⁺ | | % xyl⁺ among met⁺ | | Stable: unstable | Transposon loss |
| S. typhimurium: | | | | | | |
| mut⁺ | 7.7 | (389) | 5.8 | (412) | 33:1 | |
| mutL::Tn10 | 3.6 | (412) | 9.4 | (412) | 8:27 | 7/8, 0/27 |
| mutS::Tn10 | 8.7 | (412) | 6.6 | (375) | 1:34 | 0/1, 0/34 |
| mutH::Tn5 | 10.7 | (412) | 1.9 | (412) | 7:28 | 0/7, 0/28 |
| mutU::Tn5 | 2.4 | (412) | 22.0 | (412) | 19:16 | 19/19, 3/16 |
| E. coli: | | | | | | |
| mut⁺ | 63.1 | (412)* | 18.9 | (412)* | 20:0 | |

To assess whether Escherichia mut⁺ genes ever replaced Salmonella mut genes, we monitored the Tn insertions in the Salmonella mut genes: if the functional E. coli mut⁺ gene replaced the resident Tn-bearing mut gene. Then the recombinant will have lost both its Tn⁻ borne drug resistance and its mutator character. This has indeed happened for 7 out of 8 stable xyl+ met⁺ recombinants from the cross with S. Typhimurium mut L::Tn10 as the recipient, suggesting that, except for one recombinant, Escherichia sequences replaced Salmonella sequences for about 5 min beyond the last selected gene (met A) into the mut L region. In the cross with S. Typhimurium mut:: Tn5 as the recipient, the mut U gene was replaced in 19 out of 19 stable xyl⁺ recombinants. None of the xyl⁺met⁺ recombinants from mut S::Tn10 and mutH::Tn5 crosses showed transposon loss or mut gene replacement because mating was interrupted at 40 min and the mutS mutH chromosomal region of genes would therefore not be transferred.

Evidence for physical linkage between Salmonella and Escherichia genome sequences is shown in FIG. 1. Genomic DNA of the two parental strains and of three stable intergeneric xyl⁺met⁺ recombinants (from mutL, mutS and mutH crosses respectively) was cut by the SpeI enzyme and the fragments separated by pulse field gel electrophoresis on a Beckman Gene Line TAFE apparatus. The two largest parental S. Typhimurium F⁻ DNA fragments (Δ) are absent in all three recombinants which instead have acquired at least one non parental fragment (*) that we presume contains an interspecies DNA junction. In addition, at least one large E. Coli Hfr DNA restriction fragment (∇) is found in the recombinants L17 and S12 (L17 is the recombinant which has been deposited under the number I832).

The strain of S. Typhimurium used F⁻mutL has been deposited under the reference SL4213 mutL. (no I831)

An intergeneric recombinant E. Coli Hfr/S. Typhimurium F⁻ mutL has also been deposited under the reference SCL17.

EXAMPLE 2

Heterospecific recombination in the histidine operon: replacements of Salmonella genes by Escherichia genes.

The experimental strategy to measure the frequency of gene replacement by heterospecific recombination between *Salmonella typhimurium* and *Escherichia Coli* has been the following:

1). we used as the genetic information recipient strain an *S. Typhimurium* LT2 deficient for two genes for which the functional recovery by recombination will be looked for. The hisD::IS200 mutation makes the cell his$^-$ (deficient for histidine synthesis even in the presence of an intermediate the histidinol) and proAB47 is a deletion which makes the strain deficient for the prolinesynthesis (pro$^-$) (refs Lam, S. and Roth, J. F. (1983) Cell 34 951–960; Csonka, L. N. (1981) Mol. Gen. Genet. 182 82–86). His D::IS200 corresponds to the insertion of an inactivated transposable element and thus never reverses towards hisD$^+$.

The genetic information donor strain is either an *S. typhimurium* with intact histidine and proline operons (his$^+$, pro$^+$) or an *S. typhimurium* deleted for the his operon (his 644) but made his$^+$ by the acquisition of an *E. Coli* episome F' 150 his$^+$ carrying the his operon of *E. Coli* (refs Hartman et al (1971) Adv. Genet. 16 1–34; Law, K. B. (1973) Bact. Rev. 36, 587–607).

2) The genetic transfer from the donor to the recipient is made by a transducing bacteriophage P22Hft int3 (Schnieger, H. (1972) Mol Gen. Gent. 119 75–88). This is a classical gene transfer method (for ex: Miller J. H. "Experiments in Molecular Genetics" Cold Spring Harbor Laboratory, N.Y. 1972). A phage stock is made by growth on a donor strain and then a recipient strain is infected at a multiplicity of infection inferior to 1 per bacterium and the infected bacteria are spread on "selective" plates on which only grow the bacteria which acquired the genetic character of the donor: For example M63 minimum medium (Miller) on one side with proline but without histidine and with histidinol (30 µq/ml) to detect the his D$^+$ bacteria and, on the other side, with histidine (and arginine) but without proline to detect the pro$^+$ bacteria. Roughly one phage particle out of $10^5$ carries a given gene of the donor strain due to the accidental but regular packaging of a fragment of the chromosomal DNA of the host bacteria.

One way to see the difference between homeologous (intergeneric) versus homologous (intraspecific) recombination is to determine the ratio of transductants his D$^+$ and pro$^+$ for a lysate of P22 Hft int3 coming either from the donor his D$^+$ of *E. Coli* or from the donor his D$^+$ of *S. Typhimurium* (the two strains have the same proAB genes from Salmonella)—Table 3 shows those two ratios his D$^+$/proAB$^+$ (heterospecific and homospecific), for the wild type (mut$^+$) recipient, the mutL, mutS, mutU and mutH. It can be seen that, for an heterospecific his D, the ratio hisD$^+$/proAB$^+$ increases more than a hundred times in the bacteria mutS and mutL whereas mutH increases a little less and mutU very little. When the donor is a his D$^+$ or proAB$^+$ gene of Salmonella, the ratio does not change more than 4 times. These results thus corroborate those of conjugation but in a qualitative way.

Gene replacement is shown here by using, as a genetic member of the deficiency hisD, a defective transposon Tn 10-dCam coding for the resistance to chloramphenicol (10 µg/ml) and having destroyed the hisD function by insertion in the gene (Eliott, T. and Roth, J. R. 1988 Mol. Gen. Genet. 213 332–338). The replacement of the defective hisD::Tn10 d-Cam by the functional hisD+ of *E. Coli* will have two coincidental. phenotypic effects:

i) the recipient bacteria become hisD$^+$ (grow in presence of histidinol)

ii) they lose their Tn10-dCam transposon and become sensitive to chloramphenicol.

Table 3 shows that none of the hisD$^+$ transductants have retained the chloramphenicol resistance whereas the pro$^+$ transductants kept their chloramphenicol resistance (The pro AB genes are far away from the hisD gene).

TABLE 3

Transduction crosses

A. Mutator alleles enhance the ability of *E. coli* sequences to donate histidinol prototrophy to *S. typhimurium*:

| mut allele of recipient strain | Heterospecific crosses Hol$^+$: *E. coli* Pro$^+$: *S. typhimurium* Hol$^+$/Pro$^+$ (× 10$^4$) | Homospecific crosses Hol$^+$: *S. typhimurium* Pro$^+$: *S. typhimurium* Hol$^+$/Pro$^+$ |
|---|---|---|
| mut$^+$ | 4 | 320 |
| mutL #1 | 355 | 180 |
| mutL #2 | 147 | 150 |
| mutS #1 | 696 | 130 |
| mutS #2 | 451 | 160 |
| mutU #1 | 20 | 460 |
| mutU #2 | 10 | 520 |
| mutH #1 | 37 | 180 |
| mutH #2 | 170 | 190 |

B. Interspecific transduction by allelic replacement:

| mut allele of recipient strain | Plate contains | Plate selects | Mean no of colonies |
|---|---|---|---|
| mut$^+$ | Pro, Hol | Hol$^+$ | 5 |
| | Pro, Hol, Cam | Hol$^+$ Cam$^r$ | 0 |
| | His, Arg | Pro$^+$ | 478 |
| | His, Arg, Cam | Pro$^+$ Cam$^r$ | 498 |
| mutS | Pro, Hol | Hol$^+$ | 168 |
| | Pro, Hol, Cam | Hol$^+$ Cam$^r$ | 0 |
| | His, Arg | Pro$^+$ | 1344 |
| | His, Arg, Cam | Pro$^+$ Cam$^r$ | 1110 |

EXAMPLE 3

Inactivation by transient saturation of the mismatch repair system

The error correction system (Mut H, L, S and U) is limited in *E. Coli* and can be saturated by titration that is by functional inactivation of the Mut L protein. The more powerful mutator know in *E. Coli* (mut D5) is deficient for the proofreading activity of the DNA polymerase III and, thus, produces a lot of replication errors. By transfection with an heteroduplex DNA of phage $\phi X17_4$ or $\lambda$ we have shown that in log phase in rich medium these bacteria are deficient in mismatch repair. But if the bacterial DNA replication is stopped (stationary phase or specific arrest of replication by thermosensitive mutation) the repair activity is totally recuperated. This repair is blocked if de novo protein synthesis is blocked by chloramphenicol. Thus the Mut System is not only saturated but "dead" and repair enzymes have to be re synthesized.

An in vivo mismatch repair test uses as substrate molecules specifically constructed in vitro by DNA strand separation and reconstitution of new duplexes of the heteroduplex type. Using mutant genes of specific sequence, it is possible to construct molecules with a unique given mismatch. We have used a mutant of the CI gene coding for the λ bacteriophage repressor, the protein responsible for the prophage state of the bacteriophage which gives a clear phenotype to the plaques in contrast to the turbid plaques formed by the wild type bacteriophage. We used the UV23 mutation which corresponds to an AT instead of a GC at the 43rd base pair of the CI gene. We thus constructed two DNA duplexes with one wild type strand and one strand bearing the UV23 mutation; those two duplexes are otherwise normal on roughly 5000 bp except for the mismatch GT or AC at the site of the UV23 mutation. The phage λ stock preparation and the strand separation in cesium chloride gradient in presence of poly (U,G) polymer (uridine and-guanosine have been described by Meselson and Yuan (ref. 10). As the mismatch repair system is directed by the methylation (6 methyladenine) of the 5' GATC sequences (Redman and Wagner (ref. 11), we constructed a DNA heteroduplex that is methylated on a single strand DNA is introduced as a single copy in the bacteria E. Coli treated by the calcium chloride procedure to make them permeable to external DNA (exponentially growing bacteria are kept in 0.1M $CaCl_2$ on ice for at least 2.5 h, (Mendel and Miga (ref. 12)). Transfected bacteria are spread with soft agar on Petri dishes, incubated during the night and the phage progeny of each heteroduplex molecule is determined by restreaking the phages of each infective center. Three types of infective center can be observed: pure turbid ($c^+$). pure clear (c) and mixed containing $c^+$ and c phages. Mixed infective center contain the progeny of a non repaired DNA heteroduplex. The two strands (one $c^+$ and the other c) have been replicated and have given a progeny before the repair of the mismatched bases thus giving the $c^+$ or c phenotype.

An important number of mixed infective centers indicate that there has been few repair and reciprocally. Moreover the directed repair produces pure infective centers of the type corresponding to the methylated strand and there is an incidence on the ratio $c/c^+$ (See Table 4). This methodology has been described in PNAS by Dohet and Wagner (ref. 13).

Table 4 shows that in a mutator mut D5 strain deficient in the DNA synthesis fidelity and thus producing a lot of mismatches during replication of its DNA, the mismatch repair is deficient.

TABLE 4

Genetic analylis of the phage progeny of bacteriophage λ
hemimethylated heteroduplex molecules in different
strains and conditions of growth.

| E. coli Strains | Culture Conditions | Heterduplex: $C^+$—G—(r) me$^-$ C—T—(l) me$^+$ Progeny: | | |
|---|---|---|---|---|
| | | $c^+$ | $c/c^+$ | c (%) |
| W 3110 | 32° | 0 | 4 | 96 |
| (mut$^+$) | 42° | 1 | 4 | 95 |
| C$_{600}$ (mutL) | 32° | 1 | 86 | 13 |
| | 42 | 1 | 92 | 7 |
| W 3110 | 32° | 0 | 3 | 97 |
| dna A (ts) | 42° | 0 | 3 | 97 |
| KD 1079 | 32° | 0 | 48 | 52 |
| (mut D5) | 42 | 1 | 49 | 50 |
| KD 1079 dna A (ts) | 32° | 1 | 48 | 51 |
| mut DS | 42° | 0 | 10 | 90 |

Comparing the 3% of infective centers of the W3110 dna ATs with the 48 and 49% of infective centers of the muD5 bacteria, it clearly appears that the mismatch repair is deficient in the mutator mutD5. Comparing the 49% of infective centers with the 86 to 91% in the mutL mutant, it appears that the mismatch repair deficiency is not total. The arrest of the DNA replication initiation in the mutant dna ATs at 42° C. for 2h has not affected the mismatch repair of strains other than mut D5 dna Ats where we observed the recovery of the mismatch repair with 10% of mixed infective centers. This recovery does not occur in presence of a protein synthesis inhibitor (i.e. 100 µg/ml chloramphenicol). Thus by stopping the production by error prone replication of mismatches, the repair is only recovered after protein synthesis. This suggests that the mismatch repair implies an enzymatic "suicide". Saturation would thus correspond to a functional inactivation of one or several Mut protein. In the experiments described below we show that the missing functional protein is the protein Mut L.

Preparation of the circular heteroduplex molecule of M13 mp2phage

Phage and intracellular DNA are prepared by CsCl centrifugation in presence of Ethidium bromide as described by Brooks et al (88) from purified phage or after phage infection and incubation of 30 min. These are standard procedures described by Maniatis et coll. (ref.9).

Heteroduplex is prepared by hybridation of a double strand molecule (RFI) linearized with the enzyme Ava II and denatured 10 minutes at 70° C. in water and then renatured with single strand DNA for 10 min at 60° C. in 2×SSC buffer. The single strand DNA is eliminated by the benzoyl naphthoyl cellulose in 0.1M NaCl. The heteroduplex DNA with a G:T mismatch is kept in Tris 0.05M and EDTA 0.001M at pH8. The mismatch G:T has the following genetic composition:

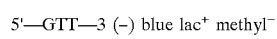

5'—GTT—3 (-) blue lac$^+$ methyl$^-$

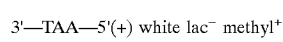

3'—TAA—5'(+) white lac$^-$ methyl$^+$

As before for the λ DNA a single molecule enters the cell made permeable by the Hanaham method (ref. 9) based on the effect of the dithiothreitol calcium and dimethylaulfoxide on the cellular walls. The transfected bacteria are diluted and spread with the indicative bacteria CSH50 (del lac-pro, ara$^-$,pro$^-$,strA) in presence of Xgal and IPTG to allow a blue coloration of the lac$^+$ plaques and not of lac$^-$ plaques (mutant); the mixed (white/blue) plaques indicate a non repaired heteroduplex.

The Table 5 below shows that when bacteria are in log phase the proportion of mixed infective centers is the same for the mutL mutant deficient in repair and the mutD mutant. But in late log phase just before stationary phase the proportion of mixed infective centers in the mutD mutant is the same as for the wild type mut$^+$. Thus the mutator mutD is deficient in mismatch repair during rapid growth but it recovers its repair activity when the growth slows down.

TABLE 5

Phage progeny of M13 mp2 bacteriophage heteroduplex molecules (heteroduplex with a G:T mismatch) in mutator strains. Effect of the growth phase.

| E. coli | nature and percentage of infective centers | | | | | | | |
|---|---|---|---|---|---|---|---|---|
| | early log phase mixed | | | | late dog phase | | | |
| strains | mixed | white | blue | total | mixed | white | blue | total |
| KA 796 (mut⁺) | 0.5 | 92 | 7.5 | 1120 | 6.9 | 76 | 17.1 | 1290 |
| NR 9163 (mutL) | 50.6 | 7.9 | 41.5 | 860 | 47.8 | 6.6 | 45.6 | 1603 |
| NR 9066 (mutD) | 40.7 | 22 | 37.3 | 1013 | 7.5 | 69.8 | 22.5 | 1949 |

The Table 6 shows that in the presence of cloned and overexpressed genes the mismatch repair activity can be recovered in the strain mutD. Specifically the mutL and mutH genes and not the mut S and mut U cloned in the plasmid pBR325 can cause the recovery of almost the total repair activity when introduced in the mutD strain. Consistent with this observation, the spontaneous mutation frequency decreases in the mutator mutD strain carrying the plasmid pBR325 (mutL⁺) or (mut H⁺ and not with the pBR325 (mutS⁺) or (mutU⁺) as is shown in Table 7.

TABLE 6

Phage progeny of M13 mp2 phage heteroduplexes (G:T mismatch) in the mutator mutD5 strain carryig plasmids with the genes mutH, mutL, mutS and mutU.

| E. coli | Nature and percentage of infective centers | | | |
|---|---|---|---|---|
| Strains | mixed | white | blue | total |
| NR 9066 mutD5 | | | | |
| without pBR | 47.8 | 17.7 | 34.4 | 661 |
| + pBR (mutH⁺) | 6.0 | 77.6 | 16.4 | 1756 |
| + pBR (mutL⁺) | 1.3 | 73.3 | 26.2 | 872 |
| + pBR (mutS⁺) | 49.8 | 14.1 | 36.0 | 1186 |
| + pBR (mutU⁺) | 39.7 | 18.5 | 41.6 | 867 |
| Segregating (mutL⁺) | 55.0 | 11.6 | 33.4 | 1161 |
| KA 796 (mut⁺) | 2.6 | 80.3 | 16.9 | 1778 |
| NR 9163 (mutL⁻) | 48.2 | 6.2 | 45.5 | 1811 |

TABLE 7

Spontaneous mutation frequencies in mutD5 carrying the plasmids pBR325 (mutH, mutL, mutS or mutU)

| | Mutation frequencies ($\times 10^{-6}$) | |
|---|---|---|
| E. coli | Rif$^R$ | Nal$^R$ |
| NR 9066 mutD5 | | |
| Without pBR | 215.0 | 60.3 |
| + pBR (mutH⁺) | 42.4 | 8.7 |
| + pBR (mutL⁺) | 15.3 | 0.71 |
| + pBR (mutS⁺) | 149.0 | 37.3 |
| + pBR (mutU⁺) | 165.0 | 36.4 |
| Segregating Amp$^S$ (mutL⁻) | 245.0 | 55.1 |
| KA 796 (mut⁺) | 0.006 | 0.0008 |

These experiments are the first experimental proof of error catastrphy or avalanche effect. An error excess at the level of DNA synthesis causes the saturation (inactivation) of the mismatch repair system. The result is a double defect in the replication fidelity system. We shoved by introducing the plasmids mutH⁺, mutL⁺, mutS⁺ and mutU⁺ in E. Coli mut D5 that there is no repair activity loss when the MutL protein is overproduced. The MutL protein thus commits "suicide" in the act of repair. The mutator mutD5 presents the first experimental case of "error catastrophy": too many errors at the level of DNA replication which overloads the repair system which, in turn, collapses and causes an avalanche effect. Thus it is sufficient to introduce at once an excessive number of mismatched bases in a cell for the repair system to collapse and stay inactive until the dilution of the substrate with mismatches and resynthesis of the Mut enzymes.

EXAMPLE 4

Saturation of the mismatch correction system in mammalian cells

It is difficult to isolate mut mutants of mammalian cells. They are recessive mutations and in diploid cells and thus requires simultaneous inactivation of the two copies of the same gene. Those mutants can moreover be lethal. This is due to the fact that the sequence polymorphism, particularly at the level of the diverse repetitive sequence families, is a key factor in the chromosomal stability. It is in fact due to this polymorphism that the mismatch repair system can impede all dangerous recombination between repetitive sequences (chromosomal aberrations or between homologous chromosomes (homozygotization) by mitotic recombination except the repairing recombination between sister chromatids (exchange of sister chromatids) coming from replication of a mother molecule and having an identical sequence. Three experiments have been attempted; following introduction in mouse cells of heteroduplexes carrying a lot of mismatches, we tried to determine if we could:

i) observe the appearance of chromosomal aberrations caused by the activation of recombination between diversified repetitive sequences ii) observe the appearance of mutations due to non repaired replication errors iii) target by a synthetic oligonucleotide a carcinogenic mutation and then correct it by another oligonucleotide.

1. CHO cells (Chinese hamster ovary) and NIH 3T3 cells (mouse fibroblasts) have been transfected by the method described by C.Chen 14). Roughly 50% of the cells are effectively transfected by the circular heteroduplex M13/fd DNA whose preparation will be described below and some 10⁶ base pairs enter the cell and consequently 200 molecules carrying some 35000 mismatches. The metaphasic phases for the observation of condensed mitotic chromosomes are prepared according to the classical procedures described by Kinsella and Radman (ref. 15 and 16).

2. To test the mutator effect of the transfection by a heteroduplex carrying a lot of mismatches, we mix the DNA of the pcD neo plasmid (Chen 14) with the heteroduplex. This allows the selection, in the presence of 400 μg/ml of neomycin G418 of cells into which the exogenous DNA entered. Among these cells, we test the mutation frequency of resistance to 6 thioguanine or ouabaine as described by Kinsella and Radman (ref. 15).

3. Targeted and programmed mutagenesis. To allow for the entrance of synthetic oligonucleties one can use several methods as the calcium phosphate method, the electroporation and the lipsome method described by Chen 17). The technique of microinjection directly in the nucleus can also be used.

We use the mouse NIH3T3 cells for transformation and the heteroduplex M13/fd whose preparation is described below for inactivation of the mismatch correction system and the 19 mer synthetic oligonucleotide 5' GTTGGAGCT TGTGGCGTAG (The underligned T is the mutated base in many human and rodent tumors which is located in the codon 12 of the K ras oncogen). The carcinogenic character of the transformed cells is visible by the growth in focuses on a cells monolayer or by growth in soft agar. By inverse mutagenesis with the oligonucleotide 5' GTTGGAGCT GGTGGCGTAG one can genetically cure the cells.

Preparation of the M13/fd and φX174/G4 heteroduplex

We made a heteroduplex containing 30% of mismatches between bacterial phages M13 and fd. The procedure principle is the following;
- isolate the intracellular DNA/circular, double strand or RFI)
- cleave each molecular population once but at different locations in the molecule
- denature-renature
- isolate the circular DNA as described by Brooks et al (ref. 8).

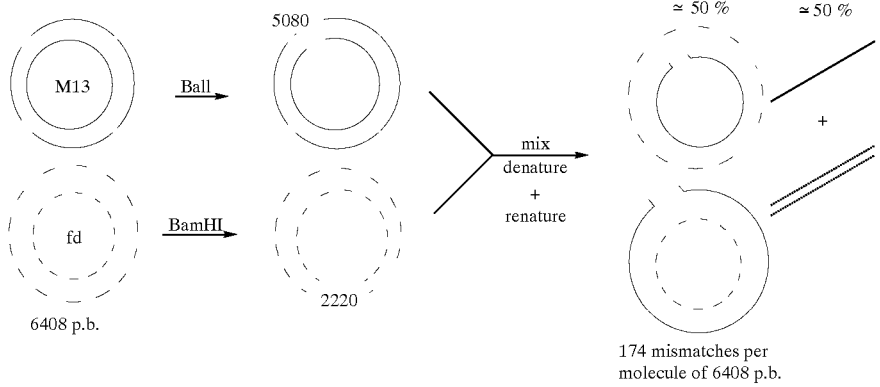

174 mismatches per molecule of 6408 p.b.

(Sequences: Van Wezenbeek et Coll. (1980) Gene, 11: 129–148)

Bacteria cultures, phage infections, isolation of the replicative form (RFI) of bacteriophages M13 or fd have been described by Messing 18) For phage M 13, the RFI is cut by BalI and, for phage fd, by BamHI. After enzymatic digestion the DNA are denatured and renatured according to the protocol described by Lee 19. After action of the *E. Coli* ligase, the covalently closed circular DNA is purified by centrifugation in CsCl Et dBr.

We also made a heteroduplex with 30% mismatches between the DNA of phages φX174 and G4 using the same procedure.

The following strains have been deposited in the "Collection Nationale de Cultures de microorganismes, Institut Pasteur, 28 rue du Docteur Roux, 75724 PARIS CEDEX 15."

| | |
|---|---|
| *Salmonella typhimurium* SL4213 mutL | n° I831 |
| Intergeneric recombinant SCL17 | n° I832 |

BIBLIOGRAPHICAL REFERENCES

1. MARINUS M. and MORRIS N. (1973) J. Bacteriol 114 1143–1150.
2. TIRABY G. and SICARD A. (1973) J. Bacteriol 1161130–1135.
3. WILLIAMSON et al. (1965) Genetics 110 609–646.
4. Ochman and Wilson in *E. coli* and *Salmonella typhimurium* Vol. 2 American Society for Microbiology Washington DC pp 1649–1654.
5. BARON et al (1959) Proc. Natl. Acad. Sci. U.S.A. 45 976–984.
6. EISENSTARK (1965) Proc. Natl. Acad. Sci. U.S.A. 54 117–120.
7. MERGEAY and GERITS (1983) J. Gen. Microbiol 129 321–335.
8. P. BROOKS et al. accepted for Proc. Natl. Acad. Sci. U.S.A.
9. Maniatis et coll. (1982) Molecules Cloning Cold Spring Harbor Laboratory.
10. Meselson and Yaun (1968) Nature 217 1110–1114.
11. Radman and Wagner (1988) Scientific American August 1988 ("Pour La Science" October 1988).
12. Mendel and Miga (1970) M. Mol. Biol 53 159–162.
13. Dohet and Wagner (1985) Proc. Natl. Acad. Sci. U.S.A. 82 503–505.
14. C. Chan, H. Okayama (1987) Mol. Cell. Biol. 7 2745–2752.
15. Kinsella and Radman (1978) PNAS 75 6149–6153.
16. Kinsella and Radman (1980) PNAS 773544–3547.
17. Biotechniques Vol 6 No 7 July/August (1988).
18. Methods in enzymology Vol 101 pp. 20–78 (1983).
19. PNAS 80 4639–4643 (1983)

We claim:

1. A process for in vivo intergeneric and/or interspecific recombination, comprising:
   combining in a cell a double-stranded DNA from a first species or genus with a double stranded DNA from a second species or genus, said first and second DNAs having sequences which are partially homologous and have mismatches able to activate the enzymatic mismatch repair system of the cell when said system is functional, wherein the enzymatic mismatch repair system is defective or has been inactivated transitorily to enable stable recombination between said DNA sequences, wherein said process is selected from the group of processes consisting of:
   (i) fusing cells of an organism of a first species or a first genus with cells of an organism of a second species or a second genus, said cells of said organism of a second species or a second genus having a defective enzymatic mismatch repair system or having said system inactivated transitorily;

(ii) crossing a unicellular organism of a first species or a first genus with a unicellular organism of a second species or a second genus, wherein at least one organism has a defective enzymatic mismatch repair system or has said system inactivated transitorily;

(iii) conjugating or transducting a recipient bacterium of a first species or a first genus and a donor bacterium of a second species or a second genus, said donor bacterium having at least one DNA sequence to be transferred to said recipient bacterium, wherein at least one of said donor bacterium and said recipient bacterium includes a defective enzymatic mismatch repair system or said system is inactivated transitorily;

(iv) inactivating said enzymatic mismatch repair system by at least one mutation of at least one of the mutS and mutL genes; and (v) placing into a unicellular organism defective or inactivated in the enzymatic mismatch repair system two DNA sequences, said two DNA sequences being partially homologous genes derived from two different organisms, and selecting the desired hybrid sequence, gene, or product thereof.

2. The process of claim 1 wherein there is produced a hybrid gene and its encoded protein, by placing into a unicellular organism defective or inactivated in the enzymatic mismatch repair system two DNA sequences, said two DNA sequences being partially homologous genes derived from two different organisms, and selecting the desired hybrid gene or its coded protein.

3. The process of part (v) of claim 1, wherein each DNA sequence is contained within a separate plasmid, wherein each plasmid is introduced into a bacterium which includes a defective or inactivated mismatched DNA repair system.

4. The process of claim 1 comprising combining (i) DNA of cells of an organism of a first species or a first genus with (ii) chromosomal DNA of cells of an organism of a second species or a second genus, said cells of an organism of a second species or a second genus being defective in the enzymatic mismatch repair system or having said system inactivated transitorily.

5. The process of claim 1 wherein said process comprises a fusion of cells of an organism of a first species or a first genus and of cells of an organism of a second species or a second genus, said cells of said organism of a second species or a second genus having a defective enzymatic mismatch repair system or having said system inactivated transitorily.

6. The process of claim 1 wherein said process comprises a cross between a unicellular organism of a first species or a first genus and a unicellular organism of a second species or a second genus, wherein at least one organism has a defective enzymatic mismatch repair system or having said system inactivated transitorily.

7. The process of claim 1 wherein said process comprises a conjugation or a transduction between a recipient bacterium of a first species or a first genus and a donor bacterium of a second species or a second genus, said donor bacterium having at least one DNA sequence to be transferred to said recipient bacterium, wherein at least one of said donor bacterium and said recipient bacterium includes a defective enzymatic mismatch repair system or said system is inactivated transitorily.

8. The process of claim 1 wherein said enzymatic mismatch repair system is inactivated transitorily by saturation of said system with non-homologous DNA.

9. The process of claim 1 wherein said enzymatic mismatch repair system is inactivated by at least one mutation of at least one of the mutS and mutL genes.

10. The process of claim 1 wherein said partially homologous DNA sequences have up to 30% of mismatches.

11. The process of claim 1, wherein in (i), said cells are selected from the group of cells consisting of bacteria, yeast, plant, and animal cells.

12. A process for intergeneric and/or interspecific recombination, comprising:

combining in a cell a DNA from a first species or genus with a DNA from a second species or genus, wherein said first and second DNAs have sequences which are partially homologous and have mismatches able to activate the enzymatic mismatch repair system of the cell when said system is functional, wherein the enzymatic mismatch repair system is defective or has been inactivated transitorily to enable stable recombination between said DNA sequences, wherein said process is selected from the group of processes consisting of:

(i) fusing cells of an organism of a first species or a first genus with cells of an organism of a second species or a second genus, said cells of said organism of a second species or a second genus having a defective enzymatic mismatch repair system or having said system inactivated transitorily;

(ii) crossing a unicellular organism of a first species or a first genus with a unicellular organism of a second species or a second genus, wherein at least one organism has a defective enzymatic mismatch repair system or has said system inactivated transitorily;

(iii) conjugating or transducing a recipient bacterium of a first species or a first genus and a donor bacterium of a second species or a second genus, said donor bacterium having at least one DNA sequence to be transferred to said recipient bacterium, wherein at least one of said donor bacterium and said recipient bacterium includes a defective enzymatic mismatch repair system or said system is inactivated transitorily;

(iv) inactivating said enzymatic mismatch repair system by at least one mutation of at least one of the mutS and mutL genes; and (v) placing into a unicellular organism defective or inactivated in the enzymatic mismatch repair system two DNA sequences, said two DNA sequences being partially homologous genes derived from two different organisms, and selecting the desired hybrid sequence, gene, or product thereof.

13. The process of claim 12, wherein in (i), said cells are selected from the group of cells consisting of bacteria, yeast, plant, and animal cells.

* * * * *

UNITED STATES PATENT AND TRADEMARK OFFICE
CERTIFICATE OF CORRECTION

PATENT NO. : 5,912,119
DATED : June 15, 1999
INVENTOR(S) : Radman et al.

It is certified that error appears in the above-identified patent and that said Letters Patent is hereby corrected as shown below:

Title page,
Item [56], References Cited,
Line 3, "Triaby" should read -- Tiraby --;

Item [57],
Line 10, "13 Claims, No Drawings" should read -- 13 Claims, 1 Drawing --.

Signed and Sealed this

Twentieth Day of November, 2001

*Attest:*

*Attesting Officer*

NICHOLAS P. GODICI
*Acting Director of the United States Patent and Trademark Office*